United States Patent
Sierro et al.

(10) Patent No.: US 6,837,709 B2
(45) Date of Patent: Jan. 4, 2005

(54) NOZZLE PIECE FOR A HANDPIECE OF A DENTAL APPARATUS

(75) Inventors: Alexandre Sierro, Geneva (CH); Lutz Beerstecher, Borex (CH)

(73) Assignee: Ferton Holding S.A. (CH)

( * ) Notice: Subject to any disclaimer, the term of this patent is extended or adjusted under 35 U.S.C. 154(b) by 127 days.

(21) Appl. No.: 10/104,686

(22) Filed: Mar. 21, 2002

(65) Prior Publication Data

US 2002/0137004 A1 Sep. 26, 2002

(30) Foreign Application Priority Data

Mar. 23, 2001 (DE) .......................................... 101 14 324

(51) Int. Cl.⁷ .................................................. A61C 3/02
(52) U.S. Cl. .......................................... 433/88; 433/80
(58) Field of Search .............................. 433/80, 88, 81, 433/82

(56) References Cited

U.S. PATENT DOCUMENTS

| | | | | |
|---|---|---|---|---|
| 4,174,571 A | | 11/1979 | Gallant | 433/216 |
| 4,412,402 A | | 11/1983 | Gallant | 433/88 |
| 4,492,575 A | | 1/1985 | Mabille | 433/88 |
| 4,676,749 A | | 6/1987 | Mabille | 433/88 |
| 4,776,794 A | | 10/1988 | Meller | 433/216 |
| 4,950,160 A | * | 8/1990 | Karst | 433/88 |
| 5,098,291 A | * | 3/1992 | Curtis et al. | 433/89 |
| 5,765,759 A | | 6/1998 | Bruns et al. | 239/398 |
| 6,439,966 B2 | * | 8/2002 | Bruns et al. | 451/38 |

FOREIGN PATENT DOCUMENTS

| | | |
|---|---|---|
| DE | 79 21 732.6 | 10/1985 |
| EP | 0 248 638 | 12/1987 |

OTHER PUBLICATIONS

Information Sheet.

* cited by examiner

*Primary Examiner*—Cary E. O'Connor
(74) *Attorney, Agent, or Firm*—Ostrolenk, Faber, Gerb & Soffen, LLP

(57) ABSTRACT

A nozzle piece for a handpiece of a dental abrasive blasting apparatus comprises a gripping member for connection with a head portion of the handpiece whereby the gripping member has a closed surface with a thusly defined curvature on its upper and underneath visual surfaces that discharge openings of two discharge nozzles of the nozzle piece are located close to a visual plane which by definition includes a longitudinal axis of the handpiece and outside of which are located the crossing points of two supply ducts with a common central axis of the two discharge nozzles, whereby the two supply ducts extend in parallel and inclined with respect to the longitudinal axis of the handpiece for defining an inclined discharge angle of a working jet of the nozzle piece.

8 Claims, 1 Drawing Sheet

NOZZLE PIECE FOR A HANDPIECE OF A DENTAL APPARATUS

FIELD OF THE INVENTION

The present invention relates to a nozzle piece for a head portion of a handpiece of a dental abrasive blasting apparatus.

BACKGROUND OF THE INVENTION

A prior art nozzle piece of the kind as herein referred comprises in general an inner discharge nozzle for discharging a mixture of a gaseous carrier medium and an abrasive dental powder as supplied by an associated first supply duct of a gripping member which is connected at an end with the head portion of a handpiece. The nozzle piece further comprises a concentrically arranged outer discharge nozzle for discharging a fluid which is supplied by an associated second supply duct of the gripping member. Nozzle pieces of this kind are disclosed for example in U.S. Pat. Nos. 4,174,571; 4,412,402 and 4,676,749 in combination with a dental abrasive blasting apparatus which comprises a powder reservoir inside of a housing of the apparatus for storing the dental powder. The nozzle piece is fixed to the one end of two tubings which directly connect with inner and outer discharge nozzles of the nozzle piece and which at their opposite end are fixed on a head piece of a gripping sleeve of the handpiece. The two tubings extend in parallel with respect to a longitudinal axis of the handpiece and are running straight or under an angle and sometimes also along a curved path towards the discharge nozzles of the nozzle piece. By these different paths of the two tubings respective different discharge angles are provided for concentric discharge openings of the inner and outer discharge nozzles which have a common central axis with respect to the longitudinal axis of the handpiece. The discharge angle is usuangle is usually in the range of 60° or more. With the provision of a discharge angle of this range any visual contact with the exit of the working jet from the discharge openings of the two discharge nozzles at the tip of the handpiece is not at all taken into consideration and it is instead only intended to reach an optimum manipulation of the handpiece for securely guiding the working jet over the preparation field of the teeth in the course of an abrasive dental treatment. The same strategy may also be recognised for dental handpieces of the kind comprising an integrated powder reservoir as for example described in U.S. Pat. No. 4,776,794 and having also a nozzle piece with inner and outer discharge nozzles for discharging a working jet over a preparation field of the teeth.

SUMMARY OF THE INVENTION

An object of the present invention is to provide a nozzle piece for a handpiece of a dental abrasive blasting apparatus which may be produced in a more simple and more inexpensive manner and which will be designed for allowing some supplemental optimization for a practical handling of the handpiece.

The present invention accordingly provides a nozzle piece which is characterised by the features as outlined in the claims.

A nozzle piece in accordance with the present invention secures a shortening of the overall length of the handpiece by the incorporation of the curved surfaces in accordance with the definition for the gripping member of the nozzle piece since thereby the visual contact with the actual preparation field of the teeth during a dental treatment is now substantially improved. The curvature as defined for the closed surface of the gripping member may be designed under ergonomic viewpoints. Different designs of the nozzle piece may also be taken into consideration especially in such a case when in accordance with an overall preferred embodiment of the present invention the gripping member comprises a metallic or plastic injection moulded part. With the provision of such an injection moulded part the gripping member could be provided at the same time with first and second bores defining the first and second supply ducts which are associated with the two discharge nozzles of the nozzle piece. At least the inner discharge nozzle would then be completed with a discharge tube which will be inserted into the associated inner bore in such a manner that the discharge opening of this discharge tube will protrude over the discharge opening of a larger diameter of the outer discharge nozzle as provided by its associated bore. A nozzle piece according to the present invention may be cleaned most easily and may be produced with low costs so that different discharge angles for the working jet with different design parameters can be envisaged all under the common aspect of optimizing the visual contact with the preparation field of the teeth.

Other objects, features and advantages of the present invention will become apparent from reading the following description of a preferred embodiment of a nozzle piece according to the present invention.

DETAILED DESCRIPTION

Figure 1:
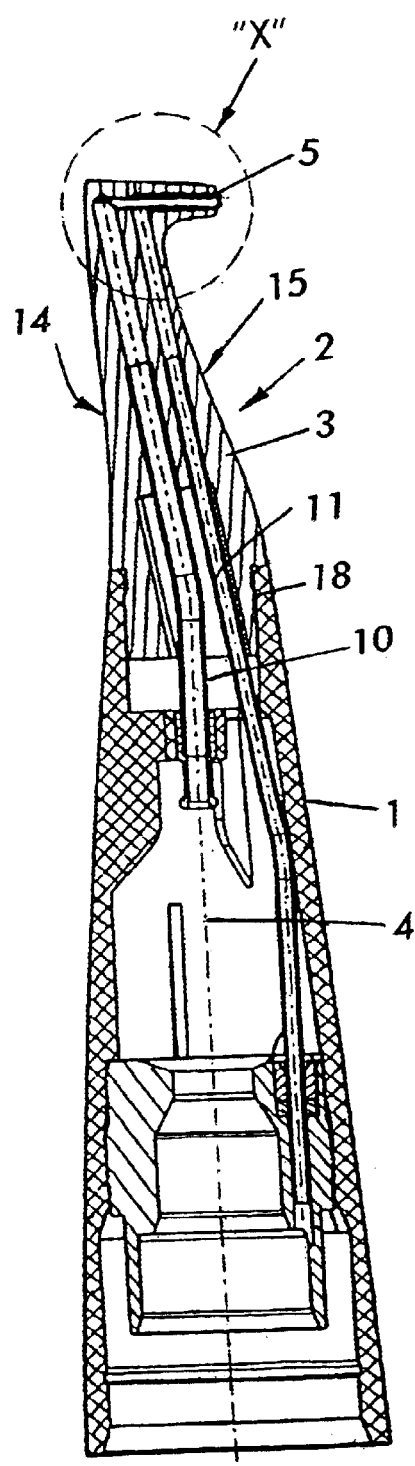
FIG. 1 is a longitudinal sectional view of the head portion of a handpiece comprising a nozzle piece in accordance with the present invention.

FIG. 1 illustrates a gripping sleeve 1 which forms the head portion of a handpiece of a dental abrasive blasting apparatus for example of the kind as more generally described in U.S. Pat. No. 4,492,575 to which reference may therefore be made for further details of the following description. The gripping sleeve 1 has a nozzle piece 2 which is exchangeably arranged on its forward end for providing a working jet when a abrasive dental treatment is applied.

The nozzle piece 2 comprises a metallic or plastic injection moulded part and has a gripping member 3 the closed surface of which is provided by definition with a curvature mainly in respect to a definite longitudinal axis 4 of the handpiece and also with respect to a central axis 5 of a jet arrangement of the jet piece 2. The central axis 5 defines a discharge angle of a working jet with respect to the definite longitudinal axis 4 of the handpiece.

Figure 2:
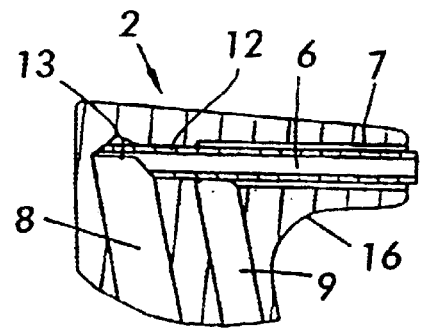
FIG. 2 shows the encircled detail X of FIG. 1 in a larger scale.

As illustrated in more detail in FIG. 2 the jet arrangement of the nozzle piece 2 comprises an inner discharge nozzle 6 for discharging a mixture of a gaseous carrier medium, namely compressed air in general, and an abrasive dental powder. It further comprises a concentrically arranged outer discharge nozzle for discharging a fluid which in general is water. The working jet is accordingly composed of a mixture of air and powder as supplied by an associated first supply duct 8 and of water as supplied by an associated second supply duct 9 whereby the water jet which is discharged from the outer discharge nozzle 7 surrounds the air and powder jet which is discharged from the inner discharge nozzle 6. The working jet which is composed of these components will be directed towards a preparation field of the teeth during an abrasive dental treatment.

Figure 3:
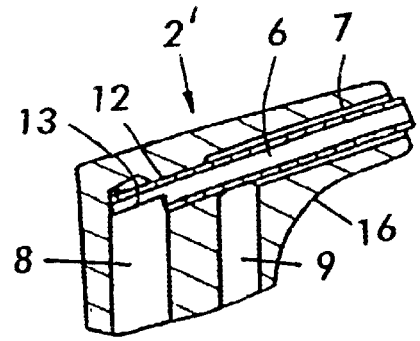
FIG. 3 shows the encircled detail X of FIG. 1 according to a second embodiment of the present invention.

The two supply ducts 8 and 9 of the two discharge nozzles 6 and 7 comprise stepped bores extending in parallel and directed under an angle with respect to the longitudinal axis 4 of the handpiece which differs from 90°. The larger diameter at the proximal end of these stepped bores serves a plug-in connection of an associated connecting line 10 and 11 connected with the two supply ducts for supplying the nozzle piece with the air and powder mixture and with water. The two discharge nozzles of the nozzle piece 2 also comprise bores whereby the inner discharge nozzle 6 is completed with a discharge tube 12 which is inserted into the associated inner bore. The discharge tube 12 has a slanted cut at its distal end 13 which protrudes into the bore of the associated supply duct 8 so that with this slanted cut of the discharge tube 12 a substantially low loss directional diversion of the air and powder mixture is obtained which is further transmitted to the discharge tube 12 the discharge opening of which protrudes over the surrounded discharge opening of the outer discharge nozzle. The discharge angle of the working jet which is discharged from a thusly designed nozzle piece is in the range of about 90° with respect to the definite longitudinal axis 4 of the handpiece in case of the embodiment illustrated in FIG. 2 and it is in the range of about 120° for the embodiment illustrated in FIG. 3.

The gripping member 3 has a closed surface which by definition is provided with such a curvature that the discharge openings of the inner and outer discharge nozzles 6 and 7 are located close to a visual plane which is in common with the longitudinal axis 4 of the handpiece. By reference to this visual plane provision is also made that the two supply ducts 8 and 9 extending in parallel along the gripping member 3 under an angle with respect to the longitudinal axis 4 of the handpiece which differs from 90° provide axial crossing points with the common central axis 5 of the two discharge nozzles 6 and 7 at locations outside of this visual plane which by definition will allow a direct visual contact with the preparation field of the teeth during an abrasive dental treatment.

Figure 4:
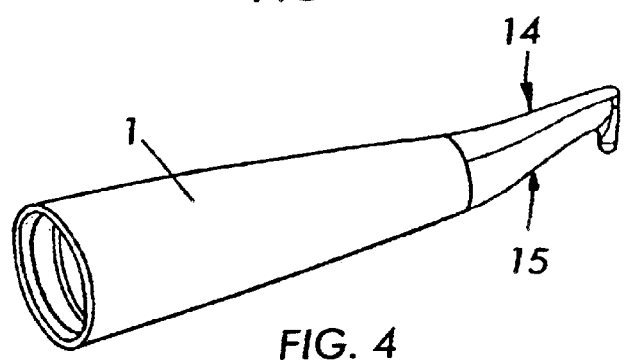
FIG. 4 is a perspective view of the head portion shown in FIG. 1 and illustrated true to scale.

For optimizing this visual contact the closed surface of the gripping member 3 is therefore provided on an upper visual face 14 with a substantially concave curvature and on an underneath visual face 15 with a substantially convex curvature. The convex curvature of the underneath visual face 15 further extends to a concave curve 16 at a transition to the discharge openings of the inner and outer discharge nozzles 6 and 7. By way of the illustrations in FIGS. 2 and 3 it should be noted that the concave curve 16 is relatively shallow with the larger discharge angle of a nozzle piece 2' according to a second embodiment of the present invention and also extends much further than the concave curve 16 which is provided with a smaller discharge angle. As further illustrated in FIG. 4 it should also be noted that the concave curvature of the upper visual face 14 provides an ergonomically designed finger resting surface by which an improved guidance of the handpiece may be obtained including a more optimized guidance of the working jet which is directed towards a preparation field of the teeth during an abrasive dental treatment. It should further be noted that by the thusly designed curvature of the closed surface of the gripping member 3 also a relatively short design length and design height of the entire nozzle piece 2 is obtained which will guarantee a perfect visual contact with the preparation field of the teeth.

Figure 5:
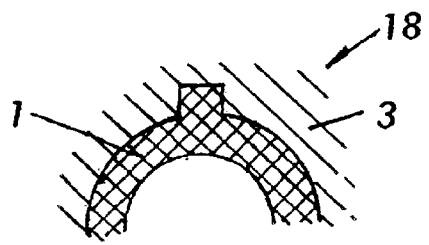
FIG. 5 is a cross-sectional detail showing a preferred embodiment of a plug-in connection.

For obtaining such a perfect visual contact for each nozzle piece 2 when fixed to the gripping sleeve 1 forming the head portion of the handpiece there is further provided a plug-in connection 18 for the two members which comprises for example a (see FIG. 5) groove and tongue connection which will secure a correct positioning of the visual plane with respect to the definite longitudinal axis 4 of the handpiece. It should be understood that instead of such a groove and tongue connection also differently designed safety means could be envisaged.

We claim:

1. A nozzle piece for a head portion of a handpiece of a dental abrasive blasting apparatus, comprising:

an inner discharge nozzle for discharging a mixture of a gaseous carrier medium and an abrasive dental powder as supplied by an associated first supply duct of a gripping member which is connected at an end with a head portion of the handpiece, a concentrically arranged outer discharge nozzle for discharging a fluid as supplied by an associated second supply duct of said gripping member, said inner and outer discharge nozzles having inner and outer discharge openings of a common central axis which by definition is inclined with respect to a longitudinal axis of the handpiece under a discharge angle in the range of 60° or more, said gripping member being provided with a closed and thusly curved surface that the first and second discharge openings of the inner and outer discharge nozzles are located close to a visual plane which is in common with the longitudinal axis of the handpiece whereby the first and second supply ducts extend in parallel along the gripping member and under an inclination angle with respect to the longitudinal axis of the handpiece which differs from 90°, said supply ducts defining axial crossing points with the common central axis of the first and second discharge openings of the inner and outer discharge nozzles which are located outside of said visual plane;

wherein the first supply duct of the gripping member is provided with a slanted transition in respect to the associated inner discharge nozzle resulting in a low loss directional diversion of the supplied mixture of a gaseous carrier medium and a dental powder towards the discharge opening of the inner discharge nozzle; and wherein said slanted transition is formed by a slanted cut of the distal end of the discharge tube which is inserted into the inner bore defining the inner discharge nozzle and which protrudes with its distal end into the associated first supply duct.

2. A nozzle piece according to claim 1, wherein the first supply duct of the gripping member is provided with a larger cross section than the associated inner discharge nozzle at a position upstream of its axial crossing point with the common central axis of the discharge openings of the inner and outer discharge nozzles.

3. A nozzle piece according to claim 1, wherein the gripping member is connected with the head portion of the handpiece by a separate plug-in connection which is thusly formed that maintenance of the visual plane is secured when nozzle pieces of a different discharge angle are connected with the head portion of the handpiece.

4. A nozzle piece according to claim 3, wherein the separate plug-in connection comprises a groove and tongue connection between the head portion of the handpiece and the gripping member for securing a correct positioning of the visual plane also for gripping members of different discharge angles.

5. A nozzle piece according to claim 1, wherein the closed surface of the gripping member is provided with an upper concavely curved visual face and an underneath visual face of a convex curve which further extends to a concave at a transition to the discharge openings of the two discharge nozzles.

6. A nozzle piece according to claim 1, wherein said gripping member comprises a metallic or plastic injection moulded part.

7. A nozzle piece according to claim 6, wherein said injection moulded part is provided with first and second bores defining said first and second supply ducts and with inner and outer bores defining said inner and outer discharge nozzles whereby at least said inner discharge nozzle is completed with a discharge tube which is inserted into the associated inner bore in such a manner that its discharge opening protrudes over the concentric discharge opening of the outer discharge nozzle.

8. A nozzle piece according to claim 7, each of said first and second bores of the gripping member comprises a stepped bore having each a larger diameter at a proximal end for allowing a plug-in connection of an associated supply line extending through the handpiece.

* * * * *